US005798434A

United States Patent [19]
Kigawa et al.

[11] Patent Number: 5,798,434
[45] Date of Patent: Aug. 25, 1998

[54] MONOMER MIXTURE AND METHOD FOR THE PREPARATION THEREOF

[75] Inventors: Hitoshi Kigawa; Hiroshi Yamagishi; Noriko Suzuki; Yoshikazu Asao, all of Tokyo, Japan

[73] Assignee: Lion Corporation, Tokyo, Japan

[21] Appl. No.: 702,589

[22] PCT Filed: Mar. 15, 1995

[86] PCT No.: PCT/JP95/00423

§ 371 Date: Aug. 30, 1996

§ 102(e) Date: Aug. 30, 1996

[87] PCT Pub. No.: WO95/25133

PCT Pub. Date: Sep. 21, 1995

[30] Foreign Application Priority Data

Mar. 16, 1994 [JP] Japan ................................. 6-71539

[51] Int. Cl.$^6$ ................................................. C08G 63/52
[52] U.S. Cl. ..................... 528/306; 528/272; 528/295.3; 568/591; 568/594; 568/606; 568/623
[58] Field of Search .................... 528/272, 295.3, 528/306; 568/591, 594, 606, 623

[56] References Cited

U.S. PATENT DOCUMENTS

| | | | |
|---|---|---|---|
| 5,250,494 | 10/1993 | Wehrmann et al. | 503/227 |
| 5,556,557 | 9/1996 | O'Brien et al. | 210/787 |
| 5,563,206 | 10/1996 | Eicken et al. | 524/590 |

FOREIGN PATENT DOCUMENTS

| | | |
|---|---|---|
| 0146089 | 6/1995 | European Pat. Off. . |
| 04346349 | 10/1991 | Japan . |
| 3236349 | 10/1991 | Japan . |
| 04077514 | 3/1992 | Japan . |

OTHER PUBLICATIONS

Coenen, "Catalytic Processes in the Area of Industrial Fatty Acid Products," General Review Journal, 1975, vol. 77, No. 12, pp. 461–467 (and English abstract).
Supplementary European Search Report.

*Primary Examiner*—Samuel A. Acquah
*Attorney, Agent, or Firm*—Burns, Doane, Swecker & Mathis, LLP

[57] ABSTRACT

A monomer mixture having a hydroxyl value ranging from 0 to 134 KOH mg/g, obtainable by polymerizing a mixed raw material of an unsaturated compound selected from the group consisting of fatty acids each having one carboxyl group and one double bond in the molecule and having 11 to 22 carbon atoms and lower alkyl esters thereof with an unsaturated compound selected from the group consisting of fatty acids each having one carboxyl group and 2 to 4 double bonds in the molecule and having 11 to 22 carbon atoms and whose iodine value ranges from 30 to 130 g (iodine)/100 g to give dimers and trimers, then converting the carboxyl groups (or the lower alkyl ester group in case of the lower alkyl esters) present in the resulting dimers and trimers into hydroxyl groups through reduction to give a mixture substantially consisting of dimer diols and trimer triols, and then subjecting the mixture having a dimer diol/trimer triol weight ratio ranging from 30/70 to 99/1 to an esterification reaction with an α, β-unsaturated carboxylic acid or a transesterification reaction with a lower alkyl ester of an α, β-unsaturated carboxylic acid. The monomer mixture is useful in the synthesis of polymers such as various kinds of resin materials for optical applications.

27 Claims, No Drawings

MONOMER MIXTURE AND METHOD FOR THE PREPARATION THEREOF

TECHNICAL FIELD

The present invention relates to a monomer mixture useful for synthesizing (meth)acrylic acid ester series polymers suitably used as, for instance, various kinds of optical resin materials as well as a method for preparing the monomer mixture.

BACKGROUND OF THE INVENTION

There have been known higher aliphatic diols having not less than 20 carbon atoms. These diols are in general prepared by polymerizing a higher unsaturated fatty acid to give a mixture of dimer (dimer acid), trimer (trimer acid) and various oligomeric acids (hereinafter also referred to as "polymeric acids"); and then subjecting the mixture to a reduction treatment to thus convert the carboxyl groups present in the molecules of the foregoing dimer acid or the like into hydroxyl groups. Accordingly, the higher aliphatic diol thus prepared is a mixture comprising chain and cyclic products and the like or a plurality of compounds having different molecular weights and also comprises monohydroxy carboxylic acids and esters with the polymeric acids in addition to the diols.

Japanese Un-Examined Patent Publication (hereinafter referred to as "J. P. KOKAI") Nos. Sho 60-157106 and Hei 3-236349 propose that these higher aliphatic diols thus prepared are reacted with α, β-unsaturated carboxylic acids such as acrylic acid and methacrylic acid to give esters thereof and the resulting ester derivatives are used as raw materials for vinyl-polymerization reactions.

However, the polymers obtained through the polymerization of the foregoing esters of acrylic acid, methacrylic acid or the like with the higher aliphatic diols are insufficient in heat resistance and also insufficient in, for instance, impact resistance and flexibility.

DISCLOSURE OF THE INVENTION

It is an object of the present invention to provide a monomer mixture comprising esters of higher aliphatic polyols with α, β-unsaturated carboxylic acids, which can provide polymers having excellent heat resistance, impact resistance and flexibility.

Another object of the present invention is to provide a method for preparing the foregoing monomer mixture in high efficiency.

The foregoing and other objects of the present invention will become more apparent from the description given below and Examples.

The present invention has been developed on the basis of the following finding that the foregoing problems can be solved by the use of a monomer mixture which is prepared by polymerizing a higher unsaturated fatty acid or a higher unsaturated aliphatic alcohol, followed by the removal of the unreacted substances to give only dimer product thereof or a mixture of dimers and trimers in a specific mixing ratio and then esterifying the dimer or the mixture thereof with α, β-unsaturated carboxylic acids or subjecting it to transesterification with lower alkyl esters of α, β-unsaturated carboxylic acids.

According to a first aspect of the present invention, there is provided a monomer mixture which can be obtained by subjecting a dimer diol/trimer triol mixture selected from the group consisting of (a) dimer diol/trimer triol mixtures each substantially consisting of dimers and trimers which are prepared by polymerizing an unsaturated compound selected from the group consisting of fatty acids having, in the molecule, one carboxyl group and 1 to 4 double bonds and having 11 to 22 carbon atoms and lower alkyl esters thereof and then converting, into hydroxyl group, the carboxyl group (or the lower alkyl ester group in case of the lower alkyl esters) of the resulting dimers and trimers through reduction and having a weight ratio: dimer diol/trimer triol ranging from 30/70 to 99/1; and (b) mixtures each substantially consisting of dimer diols and trimer triols which are prepared by polymerizing an unsaturated compound selected from the group consisting of aliphatic alcohols having, in the molecule, one hydroxyl group and 1 to 4 double bonds and having 11 to 22 carbon atoms and having a weight ratio: dimer diol/trimer triol ranging from 30/70 to 99/1, to an esterification reaction with α, β-unsaturated carboxylic acids or to a transesterification reaction with lower alkyl esters of α,β-unsaturated carboxylic acids.

According to a second aspect of the present invention, there is provided a method for preparing a monomer mixture which comprises the steps of polymerizing an unsaturated compound selected from the group consisting of fatty acids having, in the molecule, one carboxyl group and 1 to 4 double bonds and having 11 to 22 carbon atoms and lower alkyl esters thereof to give a low molecular weight mixture;

then distilling the low molecular weight mixture to substantially remove the unreacted substances and to thus give a mixture substantially consisting of dimers and trimers;

converting, into hydroxyl groups, the carboxyl groups (or the lower alkyl ester groups in case of the lower alkyl esters) of the resulting dimers and trimers through reduction to thus give a mixture substantially consisting of dimer diols and trimer triols and having a weight ratio: dimer diols/trimer triols ranging from 30/70 to 99/1; and subjecting the mixture to an esterification reaction with α, β-unsaturated carboxylic acids or to a transesterification reaction with lower alkyl esters of α, β-unsaturated carboxylic acids.

BEST MODE FOR CARRYING OUT THE INVENTION

Examples of the fatty acids each having, in the molecule, one carboxyl group and 1 to 4 double bonds and having 11 to 22 carbon atoms are oleic acid, elaidic acid, octadecenoic acid, linoleic acid, palmitoleic acid, myristoleic acid, linolenic acid, isooleic acid, eicosenoic acid, docosenoic acid, branched octadecenoic acid, branched hexadecenoic acid and undecylenic acid. These fatty acids may be used alone or in any combination. These fatty acids are preferably have 14 to 20 carbon atoms and more preferably 16 to 18 carbon atoms. Preferred are those having linear chains. The fatty acids may be contaminated with fatty acids or saturated fatty acids having a carbon atom number outside the range of from 11 to 22.

Examples of the lower alkyl esters of the foregoing fatty acids are lower alkyl esters having 1 to 6 carbon atoms such as methyl esters, ethyl esters, propyl esters and butyl esters. Among these, lower $C_1$ to $C_4$ alkyl esters are particularly preferred.

Examples of aliphatic alcohols each having, in the molecule, one hydroxyl group and 1 to 4 double bonds and having 11 to 22 carbon atoms are palmitoleyl alcohol, oleyl alcohol, elaidyl alcohol, octadecenyl alcohol and eicosenyl alcohol. These aliphatic alcohols may be used alone or in any combination. These aliphatic alcohols are preferably have 14 to 20 carbon atoms and more preferably 16 to 18 carbon atoms. Preferred are those having linear chains. The aliphatic alcohols may be contaminated with alcohols having a carbon atom number outside the range of from 11 to 22.

In a case of using the foregoing unsaturated compounds, it is preferred to use a mixture comprising an unsaturated compound carrying one double bond in the molecule and an unsaturated compound carrying at least two double bonds in the molecule. In this case, it is appropriate that the iodine value thereof is adjusted to the range of from 30 to 130 g (iodine)/100 g, preferably 40 to 120 g (iodine)/100 g and more preferably 50 to 100 g (iodine)/100 g. This allows easy preparation of a polymerized product having a weight ratio: linear dimers/cyclic dimers ranging from 51/49 to 90/10 and preferably 55/45 to 80/20. In this respect, if the iodine value exceeds 130 g (iodine)/100 g, the content of cyclic dimers in the resulting monomer mixture increases, while if it is less than 30 g (iodine)/100 g, the number of double bonds present in the unsaturated compound is too small to ensure the sufficient progress of the dimerization reaction and it takes a long time period for the preparation of dimers and trimers.

The α, β-unsaturated carboxylic acids may be those having 3 to 8 carbon atoms, preferably 3 to 4 carbon atoms such as acrylic acid, methacrylic acid and crotonic acid. Among these, preferred are acrylic acid and methacrylic acid. It is also possible to use lower alkyl (having 1 to 6 carbon atoms) esters of these carboxylic acids in the present invention.

In the present invention, the foregoing unsaturated compound (a) or (b) is first polymerized to form dimers and trimers. This polymerization can be carried out using any polymerization catalyst which permits the preparation of low molecular weight polymers, but a liquid or solid Lewis acid or Brø nsted acid is preferably used as such a polymerization catalyst, with a solid acid catalyst as one of the Brø nsted acids being more preferred. Examples of such catalysts include various kinds of activated clay products such as activated clay of montmorillonite and activated clay of bentonite, synthetic zeolite, silica/alumina and silica/magnesia. The amount of such a catalyst used in the polymerization ranges from 1 to 20 parts by weight and preferably 2 to 8 parts by weight per 100 parts by weight of the foregoing unsaturated compound. The reaction temperature ranges from 200° to 270° C. and preferably 230° to 250° C. The reaction may be carried out at a reduced pressure, ordinary pressure or under an applied pressure, but the reaction pressure in general ranges from 1 to 10 atm. (as expressed in terms of the absolute pressure) and preferably 2 to 10 atm. The reaction time varies depending on the amount of the catalyst used and the reaction temperature selected, but it is in general sufficient to carry out the reaction for 5 to 10 hours. The polymerization can be performed in the open air, but preferably carried out in an inert gas atmosphere such as nitrogen gas and argon gas atmospheres in order to obtain a polymer having excellent color tone.

Then the unreacted substances are removed from the polymerized product thus obtained to give a mixture substantially consisting of dimers and trimers. In this case, the dimers and trimers are preferably isolated separately from one another, but they may likewise be isolated and recovered in the form of a mixture thereof. Examples of methods for separating dimers from trimers which may be adopted in the present invention are molecular distillation techniques, thin film distillation techniques, extraction methods, chromatographic separation techniques, separation techniques through adsorption and the like.

The conditions for separation may widely vary depending on the kind and molecular weight of the unsaturated compound used, but if methyl oleate is, for instance, used as the unsaturated compound, the resulting dimers and trimers can be separated from one another by distilling off the dimers at a temperature ranging from 250° to 280° C. (0.3 to 0.5 mmHg) while distilling off the trimers at a temperature ranging from 280° to 310° C. (0.005 to 0.01 mmHg).

The dimers obtained through the use of the unsaturated compound (a) is a mixture of linear and cyclic ones. Typical structures thereof will be listed below:

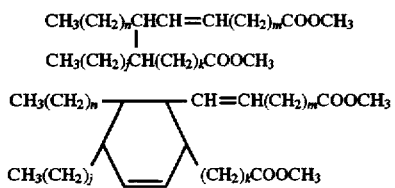

(In the formulas, j, k, m and n each represents an integer).

The trimer prepared through the use of the foregoing unsaturated compound (a) is likewise a mixture of linear and cyclic compounds which are polymers having structures more complicated than those of the foregoing dimers. The weight ratio: linear trimers/cyclic trimers is preferably the same as that defined above for the dimers.

The above descriptions concerning the foregoing dimers and trimers are also true for the dimers and trimers obtained using the unsaturated compounds (b).

The polymerization carried out using the foregoing unsaturated compounds (a) permits the formation of dimers each carrying two carboxyl groups in the molecule and trimers each carrying three carboxyl groups in the molecule, while the polymerization carried out using the foregoing unsaturated compounds (b) permits the formation of dimers each carrying two hydroxyl groups in the molecule and trimers each carrying three hydroxyl groups in the molecule.

Therefore, the polymers prepared using the foregoing unsaturated compounds (a) should then be reduced to convert the carboxyl groups present in the dimers and trimers (in case of lower alkyl esters, lower alkyl ester groups) into hydroxyl groups to give dimer diols and trimer triols.

These dimers and trimers may separately be subjected to the reduction treatment, but it is preferred to reduce the mixture thereof. The reduction methods usable herein may be those conventionally known methods such as catalytic reduction methods wherein hydrogen gas is used in the presence of a catalyst and reduction methods which make use of an agent for hydrogen-addition such as lithium aluminum hydride ($LiAlH_4$), lithium borohydride ($LiBH_4$) and sodium metal/alcohol systems.

Examples of catalysts used in the catalytic reduction method are nickel, Raney nickel, Raney cobalt, platinum black, platinum oxide, copper-chromium, copper-zinc, palladium, palladium black, and catalysts comprising hydrogen-activating metals (for instance, transition metals such as nickel, cobalt, molybdenum, platinum and palladium) supported on a porous substance such as alumina and silica. The catalytic reduction is preferably carried out at a temperature ranging from 50° to 300° C., preferably 200° to 280° C. and a hydrogen gas pressure ranging from 1 to 300 kg/cm² and preferably 150 to 250 kg/cm². The reaction time is in general in the range of from 3 to 15 hours.

In the reduction method which makes use of an agent for hydrogen-addition, the reduction is preferably carried out at a temperature equal to or higher than the hydrogen-generating temperature of the hydrogen-addition agent. For instance, the reduction is carried out at a temperature ranging from 0° to 35° C. when using $LiAlH_4$ as the hydrogen-addition agent or 20° to 50° C. when using $LiBH_4$ as the hydrogen-addition agent. The reaction temperature usually ranges from 1 to 10 hours. The rate of the hydrogen-addition agent to be used is usually 1 to 5 times the theoretical value and preferably 1.5 to 3 times thereof.

In the present invention, the unsaturated bonds present in the dimers and trimers may be converted into saturated bonds during converting the carboxyl groups present in the dimer and trimer molecules into hydroxyl groups through reduction, but it is preferred to carry out the conversion of the unsaturated bonds into saturated bonds in such a manner that the content of double bonds per dimer and trimer molecule is in the range of from 0.0002 to 2.0 (corresponding to an iodine value ranging from 0.01 to 97.6 g (iodine)/100 g), preferably 0.11 to 1.68 (corresponding to an iodine value ranging from 5.0 to 82.2 g (iodine)/100 g). This is because the rate of double bonds to be oxidized is reduced and this in turn results in, for instance, the improvement of the resulting product in stability and a decrease in the viscosity of the product.

In the present invention, when using the unsaturated compounds (b), it is not necessary to convert the carboxyl groups present in the molecule into hydroxyl groups and therefore, the products obtained through the polymerization, as such, can be used in the subsequent esterification process. Incidentally, it is preferred to carry out the conversion of a part of the unsaturated bonds into saturated bonds in such a manner that the content of double bonds per dimer and trimer molecule is in the range of from 0.0002 to 1.00 (corresponding to an iodine value ranging from 0.01 to 48.8 g (iodine)/100 g), preferably 0.01 to 0.84 (corresponding to an iodine value ranging from 0.54 to 41.1 g (iodine)/100 g) for the same reason discussed above in connection with the dimers and trimers prepared from the unsaturated compounds (a).

In the present invention, a mixture obtained by admixing the dimer diols and trimer triols prepared above or a mixture obtained by reducing a mixture of raw dimers and trimers, which has a weight ratio: dimer diol/trimer triol ranging from 30/70 to 99/1, preferably 40/60 to 95/5 and more preferably 40/60 to 90/10 is subjected to esterification reaction with an α, β-unsaturated carboxylic acid. The mixture used herein substantially consisting of dimer diols and trimer triols. Preferably, the mixture contains not more than 5% by weight and preferably not more than 3% by weight of components other than the dimer diols and trimer triols.

In the present invention, a mixture substantially consisting of dimer diols may be used and subjected to an esterification reaction with an α, β-unsaturated carboxylic acid or to a transesterification reaction with a lower alkyl ester of α, β-unsaturated carboxylic acid. The dimer diol mixture herein used has a dimer diol content of not less than 95% by weight and preferably not less than 97% by weight.

The esterification reaction of the dimer diol mixture or the dimer diol/trimer triol mixture with an α, β-unsaturated carboxylic acid or the transesterification reaction thereof with a lower alkyl ester of α, β-unsaturated carboxylic acid may be carried out in accordance with the conventional method in the presence of a catalyst for esterification and transesterification and a polymerization inhibitor.

The esterification and transesterification catalyst may, for instance, be acidic catalysts such as hydrogen fluoride, boron trifluoride, p-toluenesulfonic acid and methanesulfonic acid; basic catalysts such as lithium hydroxide, sodium hydroxide, potassium hydroxide, sodium hydrogen carbonate and sodium carbonate; and alkoxides of metals, for instance, those of aluminum, sodium, potassium, lithium and titanium with alcohols such as methanol, ethanol, propanol and butanol. The amount of the catalyst used ranges from 0.01 to 10 by weight and preferably 0.1 to 5% by weight on the basis of the total weight of the dimer diols, trimer triols and the α, β-unsaturated carboxylic acid used. Examples of such polymerization inhibitors are those commonly used such as hydroquinone, p-methoxyphenol, 6-tert-butyl-2,4-xylenol, chloranil, 2,5-dichloro-p-benzoquinone, 2,6-dichloro-p-benzoquinone, 1,1-diphenyl-2-picrylhydrazyl, p-benzoquinone, p-nitrosodimethylamine, p-nitrosodimethylaniline and phenothiazine. The amount of the polymerization inhibitor ranges from 0.0001 to 1% by weight on the basis of the total weight of the dimer diols, the trimer triols, the α, β-unsaturated carboxylic acid and the lower alkyl esters of α, β-unsaturated carboxylic acid used. The reaction temperature and time are determined while taking into consideration the balance between the reaction rate and the amount of polymers produced as by-products, but in general range from 50° to 130° C. and 1 to 10 hours, respectively. The resulting unsaturated carboxylic acid ester may, if necessary, be distilled under a reduced pressure to remove the unreacted unsaturated carboxylic acid or the ester thereof or the resulting ester may likewise be washed with an alkaline aqueous solution to remove the unreacted unsaturated carboxylic acid or the ester and purify the ester.

In the foregoing esterification reaction, the α, β-unsaturated carboxylic acid may be replaced with a lower alkyl ester thereof. In this regard, water is formed as a by-product when unsaturated carboxylic acid is used, while a lower alcohol is formed as a by-product when a lower alkyl ester of α, β-unsaturated carboxylic acid is used. Preferably, such a by-product is continuously separated and removed from the reaction system. The separation of the by-product is preferably carried out by evaporation, or passing an inert gas through the reaction system to thus separate and remove the gaseous by-product from the reaction system together with the inert gas, or by adding a solvent capable of forming an azeotropic mixture with water or an alcohol as a by-product to thus remove it in the form of an azeotropic mixture. In this connection, water or the lower alcohol as such a by-product may likewise be removed by allowing it to stand under a reduced pressure.

The amount of the α, β-unsaturated carboxylic acid or the lower alkyl ester of α, β-unsaturated carboxylic acid to be reacted with a dimer diol mixture or a dimer diol/trimer triol mixture preferably ranges from 0.33 to 5 eq. per one equivalent of the hydroxyl group present in the mixture. To substantially completely esterify the whole amount of hydroxyl groups present in the mixture, it is desirable that the α, β-unsaturated carboxylic acid be used in a rate ranging from 1.0 to 5.0 eq., preferably 1.05 to 1.5 eq. per one equivalent of the hydroxyl group present in the mixture. Moreover, if only part of the hydroxyl groups included in the mixture are esterified while leaving unreacted free hydroxyl groups, the rate of the free hydroxyl groups suitably ranges from 0.33 to 0.99 time, preferably 0.5 to 0.95 time the total equivalent of the hydroxyl groups to be esterified among the whole hydroxyl groups present in the mixture.

Among these, all of the hydroxyl groups are preferably esterified, but in practice, the resulting esterified product preferably comprises terminal free alcoholic hydroxyl groups in an amount ranging from 0.1 to 134 KOH mg/g, preferably 0.2 to 37 KOH mg/g and more preferably 0.3 to 30 KOH mg/g as expressed in terms of the hydroxyl value.

Such free hydroxyl group-containing unsaturated carboxylic acid ester monomer mixture may be polymerized to give a polymer carrying free hydroxyl groups. Such a polymer has hydrophilicity and is excellent in, for instance, adhesiveness, coating properties and dyeability because of the presence of free hydroxyl groups and it is also possible to impart any desired properties to the polymer through the reaction of the hydroxyl groups with various reactants having reactivity with hydroxyl groups.

Moreover, it is preferred that the monomer mixture prepared in the present invention have a hue of not more than 250, preferably not more than 200 and in general 20 to 150 as expressed in terms of APHA. Moreover, the viscosity thereof (as determined at 25° C. using Brookfield type viscometer) is not more than 400 cp (for instance, 70 to 400 cp), preferably not more than 350 cp and generally 70 to 330 cp. In addition, the monomer mixture in general has a broad molecular weight on the order of, for instance, 400 to 1500.

The monomer mixture of the present invention can be polymerized in the presence of a polymerization initiator according to the conventional vinyl-polymerization method to give a final product. The polymerization initiators usable herein may be azo type radical polymerization initiators such as azobisisobutyronitrile (AIBN) and azobisvaleronitrile (AVN); and peroxide type radical polymerization initiators such as benzoyl peroxide (BPO) and lauryl peroxide (LPO). In this case, it is in general preferred to carry out the polymerization in the presence of a chain transfer agent such as mercaptan which is required for adjusting the molercular weight (or the degree of polymerization). Polymerization methods usable herein are, for instance, bulk polymerization, solution polymerization, emulsion polymerization and suspension polymerization, which may be appropriately selected depending on the applications of the resulting polymers. To this polymerization reaction system, there may optionally be added other vinyl monomers such as unsaturated carboxylic acid esters of alcohols having not less than 10 carbon atoms, acrylic acid or esters thereof, methacrylic acid or esters thereof, hydroxyethyl methacrylate, styrene and divinylbenzene.

The present invention will hereinafter be described in more detail with reference to the following Examples. Incidentally, all of the terms "%" used hereunder mean "% by weight".

EXAMPLE 1

To a 2 liter-volume autoclave, there were added 1000 g of a starting higher unsaturated fatty acid ester having the composition specified in Table 1 (iodine value: 92.0 g (iodine)/100 g [total amount of the unsaturated compounds]) and 70 g of montmorillonite type activated clay as a catalyst and then the fatty acid ester was polymerized at 230° C. for 5 hours in a nitrogen gas atmosphere. After filtering the product of the polymerization reaction, the unreacted components were distilled off through thin film distillation (200 to 220° C. /0.3 to 0.5 mmHg), followed by distilling off the dimer fraction (250° to 280° C. /10.3 to 0.5 mmHg) to thus give about 450 g of dimethyl esters of dimer acids and about 150 g of trimethyl esters of trimer acids. In this respect, the structure of the resulting dimethyl ester of dimer acid was determined by the GC-MS technique after subjecting it to the same treatment used by H.H. Mcmahon et al. (J. Am. Oil Chemist Soc., 1974,51, p. 522) and as a result, it was found that the dimethyl ester comprised 70% of those having linear chain structures and 30% of those having cyclic structures.

TABLE 1

| Methyl Oleate | 75% |
|---|---|
| Methyl Linoleate | 15% |
| Methyl Stearate | 9% |
| The Rest | 1% |

Then there was admixed 225 g of the dimethyl esters of the dimer acids with 25 g of the trimethyl esters of the trimer acids to give a 9/1 (weight ratio) mixed solution of dimer/trimer.

Thereafter, the inner space of a reactor device equipped with a stirring machine, a cooling tube, a thermometer, a dropping funnel and a tube for introducing $N_2$ gas was replaced with nitrogen gas, followed by adding 32 g of lithium aluminum hydride ($LiAlH_4$), and gradually adding 1200 ml of diethyl ether through the dropping funnel at room temperature with stirring while passing nitrogen gas, in small portions, through the reactor. To the $LiAlH_4$ dispersion in diethyl ether thus formed, there was slowly and dropwise added 250 g of the dimer/trimer mixed solution prepared above which had been diluted with 350 ml of diethyl ether over about 2 hours. At this stage, the temperature of the solution rose due to the heat of reaction and therefore, the solution temperature was adjusted to a level of not more than about 30° C. by ice-cooling the solution at intervals. After completion of the dropwise addition, the mixture was ripened for 30 minutes and then 65 g of water was slowly dropwise added to the mixture through the dropping funnel. The resulting solution was slowly poured into a beaker to which 350 g of ice had been introduced. Then 250 g of a 10% aqueous sulfuric acid solution was added and thereafter, an appropriate amount of diethyl ether was added to extract the solution, i.e., to separate the ether phase. Further the ether phase was washed several times with water till the wash liquid became neutral, followed by distilling off the solvent in the resulting ether phase to give 210 g of a diol/triol mixed liquid as a transparent and viscous liquid having a pale yellow color. The iodine value of this mixed liquid was found to be 68 g (iodine)/100 g.

Then to a reaction device equipped with a stirring machine, an $N_2$-introducing tube, a thermometer, a cooling tube and a water pilot tube, there were added 210 g of the foregoing mixed liquid consisting of diols and triols, 74 g of methacrylic acid, 0.15 g of p-methoxyphenol, 1.42 g of p-toluenesulfonic acid and 120 g of cyclohexane and the content of the reaction device was heated to about 90° C. with stirring while passing air in small portions through the content. Then the esterification was continued for about 6 hours at that temperature while removing the resulting water outside the system till the amount of the water formed reached 14.0 g, followed by cooling the reaction system, dissolving in 180 g of diethyl ether, neutralization of the system with 35 g of a 1.0% sodium hydroxide solution and separation and removal of the water phase. Moreover, the ether phase was washed several times with water till the wash liquid became neutral, followed by addition of 0.15 g of p-methoxyphenol, distilling off the solvent under a reduced pressure to give 237 g of a methacrylic acid ester which was a pale yellow-colored transparent liquid. This substance has characteristic properties listed in the following Table 2.

TABLE 2

| | |
|---|---|
| Viscosity (Brookfield type viscometer, at 25° C.) | 38 cp |
| Acid Value | 0.2 KOH mg/g |
| Hydroxyl Value | 0.3 KOH mg/g |
| IR Analysis (neat), v cm$^{-1}$: 1720, 1638, 1160 | |
| NMR Analysis (in CDCl$_3$), δ (ppm) | |
| 6.11 ⎤ vinyl proton | 4H |
| 5.50 ⎦ | |
| 4.15  proton adjacent to ester | 4H |
| 1.92  methyl proton | 6H |
| 1.73–0.80  aliphatic proton | 64H |

The data listed in Table 2 clearly indicate that the foregoing reaction provides a methacrylate mixture of the dimer diol/trimer triol mixture in which almost all of the —OH groups are converted into methacrylic acid ester.

EXAMPLE 2

The starting higher unsaturated fatty acid ester having the composition specified in Table 1 was reacted in the same manner used in Example 1, followed by filtering the reaction product, then thin film distillation to give dimethyl esters of dimer acids and trimethyl esters of trimer acids, mixing 75 g of the dimethyl esters with 175 g of the trimethyl esters and then hydrogenation of the resulting mixture using lithium aluminum hydride in the same manner used in Example 1 to give a mixed liquid of diols and triols (diol/triol=30/70). The iodine value of the mixed liquid was found to be 71 g (iodine)/100 g.

When the mixture was reacted with methacrylic acid, a methacrylate which was a pale yellow-colored transparent liquid was obtained. This substance has characteristic properties shown in the following Table 3.

TABLE 3

| | |
|---|---|
| Viscosity (Brookfield type viscometer, at 25° C.) | 148 cp |
| Acid Value | 0.3 KOH mg/g |
| Hydroxyl Value | 0.4 KOH mg/g |
| IR Analysis (neat), v cm$^{-1}$: 1719, 1638, 1162 | |
| NMR Analysis (in CDCl$_3$), δ (ppm) | |
| 6.12 ⎤ vinyl proton | 6H |
| 5.55 ⎦ | |
| 4.15  proton adjacent to ester | 6H |
| 1.93  methyl proton | 9H |
| 1.73–0.80  aliphatic proton | 97H |

The data listed in Table 3 clearly indicate that the reaction provides a methacrylate mixture of the dimer diol/trimer triol mixture in which almost all of the —OH groups are converted into methacrylic acid ester.

EXAMPLE 3

To a reaction device equipped with a stirring machine, a nitrogen gas-introducing tube, a thermometer and a cooling tube, there were added 100 g of the 9/1 dimer diol/trimer triol mixture prepared in Example 1, 12 g of methyl methacrylate, 0.1 g of p-methoxyphenol and 2.0 g of tetraisopropoxy titanate. When the heating of the reaction device was initiated, distillation of methanol was started. After the reaction temperature reached 90° C., the reaction system was maintained at this temperature for 6 hours. After cooling the reaction product, a small amount of water was added thereto and TiO$_2$ precipitated was removed through filtration. Then ether and water were added to the filtrate to sufficiently wash the latter, followed by drying the resulting ether phase on Na$_2$SO$_4$ and then removal of the ether under a reduced pressure to thus give a yellow-colored liquid. This substance has characteristic properties specified in the following Table 4.

TABLE 4

| | |
|---|---|
| Acid Value | 0.4 KOH mg/g |
| Hydroxyl Value | 103 KOH mg/g |
| IR Analysis (neat), v cm$^{-1}$: 3100–3650, 1719, 1639, 1164 | |
| NMR Analysis (in CDCl$_3$), δ (ppm) | |
| 6.12 ⎤ vinyl proton | 2H |
| 5.55 ⎦ | |
| 4.15  proton adjacent to ester | 2H |
| 3.63  proton adjacent to alcohol | 4H |
| 1.92  methyl proton | 3H |
| 1.75–0.80  aliphatic proton | 97H |

The data listed in Table 4 indicate that the resulting product is an ester produced by the reaction of one —OH group of the dimer diol/trimer triol mixture with methyl methacrylate.

EXAMPLE 4

The starting higher unsaturated fatty acid ester having the composition specified in Table 1 was subjected to a polymerization reaction in the same manner used in Example 1, followed by filtering the reaction product, then removing a monomer fraction (200° to 220° C./0.3 to 0.5mmHg) and distilling off a dimer fraction (250° to 280° C./0.3 to 0.5mmHg) by the thin film distillation method to give about 450 g of dimethyl esters of dimer acids. Then the dimethyl esters of dimer acids was hydrogenated with lithium aluminum hydride in the same manner used in Example 1 to give dimer diols. The iodine value of the resulting dimer diols was found to be 65 g (iodine)/100 g. Moreover, 100 g of the dimer diol was reacted with 36 g of methacrylic acid to give a liquid pale yellow-colored transparent methacrylate. This substance have characteristic properties shown in the following Table 5.

TABLE 5

| | |
|---|---|
| Viscosity (Brookfield type viscometer, at 25° C.) | 36 cp |
| Acid Value | 0.2 KOH mg/g |
| Hydroxyl Value | 0.3 KOH mg/g |
| IR Analysis (neat), v cm$^{-1}$: 1720, 1638, 1160 | |
| NMR Analysis (in CDCl$_3$), δ (ppm) | |
| 6.12 ⎤ vinyl proton | 2H |
| 5.54 ⎦ | |
| 4.15  proton adjacent to ester | 4H |
| 1.95  methyl proton | 6H |
| 1.75–0.80  aliphatic proton | 64H |

Reference Example 1 (Preparation of Polymer)

To 10 g of the methacrylate prepared in Examples 1, 2 or 4, there was added 0.05 g of benzoyl peroxide as a polymerization initiator, followed by dissolution thereof. Then each solution was transferred to a 20 ml volume test tube, followed by holding each test tube in an oil bath maintained at 90° C. for 8 hours to give a transparent or pale yellow-colored polymer. The melting point of the resulting polymer was calculated from the heat absorption-initiating temperature observed during the DSC (RIGAKU TAS-200) measurement and found to be those listed in the following Table 6.

TABLE 6

| Ex. No. | 1 | 2 | 3 |
|---|---|---|---|
| Color Tone of Monomer Mixture (APHA) | 80 | 250 | 50 |
| Viscosity * of Monomer Mixture (cP) | 89 | 323 | 68 |
| Melting Point of Polymer (°C.) | 171 | 189 | 152 |

*: Viscosity was determined at 25° C. using a Brookfield type viscometer.

Reference Example 2

When the methacrylate prepared in Example 3 was polymerized in the same manner used in Reference Example 1, there was prepared a polymer insoluble in, for instance, acetone, toluene and ethanol. This polymer is excellent in both heat resistance and mechanical strength as compared with the polymer obtained from the methacrylate prepared in Example 4 having the characteristic properties shown in Table 6.

EXAMPLE 5

The methyl ester of higher unsaturated fatty acid shown in Table 1 as a raw material was subjected to a polymerization reaction using activated clay of montmorillonite as a catalyst in the same manner used in Example 1. After filtration of the polymerization reaction product, then removing a monomer fraction (200° to 220° C. /0.3 to 0.5 mmHg) by thin film distillation to give a mixture of dimers and trimers. The mixture was subjected to GPC analysis (column: TSK-GEL G1000HXL, available from Tosoh Corporation) using tetrahydrofuran as a solvent and it was found that the mixture comprised 71% of a dimer fraction and 29% of a trimer fraction.

Then to an autoclave equipped with a stirring machine, a thermometer and a hydrogen gas-introducing tube, there were added 1000 g of the foregoing mixture and 30 g of a copper-chromium type reducing catalyst, followed by reaction of the mixture at 250° C. for 10 hours while maintaining the hydrogen gas pressure to 220 kg/cm². The catalyst was filtered off from the resulting reaction product to give a dimer diol/trimer triol mixture. The results of the analysis of this mixture are listed in the following Table 7. The results indicate that the mixture is an alcohol compound comprising dimer diols (71%) and trimer triols (29%).

TABLE 7

| Hydroxyl Value | | 192.5 KOH mg/g |
|---|---|---|
| Ester Value | | 2.3 KOH mg/g |
| Iodine Value | | 31.2 KOH mg/g |
| IR Analysis (neat), ν cm⁻¹: 3050–3700 | | |
| NMR Analysis (in CDCl₃), δ (ppm) | | |
| 3.63 | proton adjacent to alcohol | 2H |
| 1.7–0.8 | aliphatic proton | 34H |
| GPC Analysis: | Dimer Fraction: 71% | |
| | Trimer Fraction: 29% | |

Then, to a reaction device identical to that used in Example 1, there were added 210 g of the dimer diol/trimer triol mixture, 74 g of methacrylic acid, 0.15 g of p-methoxyphenol, 2.1 g of p-toluenesulfonic acid and 120 g of cyclohexane, followed by carrying out an esterification reaction according to the same procedures used in Example 1 to give an ester compound. The ester compound was analyzed. The results thus obtained are summarized in the following Table 8. The results indicate that the ester compound thus prepared is a mixture comprising methacrylic acid esters of dimer diols (71%) and methacrylic acid esters of trimer triols (29%).

TABLE 8

| Acid Value | | 0.5 KOH mg/g |
|---|---|---|
| Hydroxyl Value | | 0.7 KOH mg/g |
| IR Analysis (neat), ν cm⁻¹: 1720, 1638, 1160 | | |
| NMR Analysis (in CDCl₃), δ (ppm) | | |
| 6.11 | vinyl proton | 1H |
| 5.50 | vinyl proton | 1H |
| 4.15 | proton adjacent to ester | 2H |
| 1.92 | methyl proton | 3H |
| 1.7–0.8 | aliphatic proton | 34H |
| GPC Analysis: | Dimer Fraction: 71% | |
| | Trimer Fraction: 29% | |

Reference Example 3

Perbutyl PV (0.1; available from Nippon Oil and Fats Co., Ltd.) serving as a polymerization initiator was added to and dissolved in 10 g of the ester mixture prepared in Example 5. Then the solution was polymerized by the method described in Reference Example 1 and the heat absorption-initiating temperature of the resulting polymer was determined by the DSC technique. The polymer was found to be insoluble in, for instance, acetone, toluene and ethanol.

On the other hand, 0.5 g each of perbutyl PV was added to and dissolved in 50 g of the ester mixture prepared in Example 5 or 50 g of the diol ester mixture prepared in Example 4, followed by injecting each solution in a glass plate of 10cm×10cm×4mm, raising the temperature to 80° C. over 30 minutes, polymerization at this temperature for 6 hours to thus give each corresponding plate-like resin molded article. The molded articles each was inspected for the following items. The results thus obtained are listed in the following Table 9.

1̂ Specific Gravity: This was determined according to ASTM D792.

2̂ Refractive Index: This was determined according to ASTM D542.

3̂ Parallel Ray Transmittance: This was determined according to JIS K7105.

TABLE 9

| | Example 5 | Example 4 |
|---|---|---|
| Heat Absorption-Initiating Temperature (°C.) | 183 | 152 |
| Specific Gravity | 0.989 | 0.991 |
| Refractive Index | 1.493 | 1.493 |
| Parallel Ray Transmittance (%) | 90.3 | 90.2 |

EXAMPLE 6

The same procedures used in Example 1 except for using a methyl ester of unsaturated fatty acid mixture having the composition specified in the following Table 10 to give about 450 g of dimethyl ester of dimer acids and about 150 g of trimethyl esters of trimer acids. The structure of the resulting dimethyl esters of dimer acids was examined by the GC-MS technique like Example 1 and it was found that it comprised 71% of those having linear chain structures and 29% of those having cyclic structures.

TABLE 10

| | |
|---|---|
| Methyl Oleate | 70% |
| Methyl Elaidate | 18% |
| Methyl linoleate | 1% |
| Methyl Stearate | 11% |

Then the resulting dimethyl esters were reduced in the same manner used in Example 1 to give 210 g of a dimer diol which was a pale yellow-colored transparent and viscous liquid. The iodine value of the dimer diol was found to be 71 g (iodine)/100 g.

Then 210 g of the dimer diol, 74 g of methacrylic acid, 0.15 g of p-methoxyphenol, 1.42 g of p-toluenesulfonic acid and 120 g of cyclohexane were introduced into a reaction device equipped with a stirring machine, an N-introduction tube, a thermometer, a cooling tube and a water-inspection tube, followed by heating with stirring up to about 90° C. while passing air in small portions through the reaction device. Then the esterification was continued for about 6 hours at that temperature while removing the resulting water out of the reaction system till the amount of the water formed reached 14.0 g, followed by cooling the reaction system, dissolving in 180 g of diethyl ether, neutralization of the system with 35 g of a 1.0% sodium hydroxide solution and separation and removal of the water phase. Moreover, the ether phase was washed several times with water till the wash liquid became neutral, followed by addition of 0.15 g of p-methoxyphenol, distilling off the solvent under a reduced pressure to give 237 g of a methacrylic acid ester which was a pale yellow-colored transparent liquid. This substance has characteristic properties listed in the following Table 11.

TABLE 11

| | | |
|---|---|---|
| Acid Value | | 0.2 KOH mg/g |
| Hydroxyl Value | | 0.5 KOH mg/g |
| IR Analysis (neat), v cm$^{-1}$: 1720, 1638, 1160 | | |
| NMR Analysis (in CDCl$_3$), δ (ppm) | | |
| 6.11 | vinyl proton | 4H |
| 5.50 | | |
| 4.15 | proton adjacent to ester | 4H |
| 1.95 | methyl proton | 6H |
| 1.73–0.80 | aliphatic proton | 64H |

The data listed in Table 11 clearly indicate that almost all of the —OH groups of the dimer diol were converted into methacrylic acid ester.

Industrial Field of Application

The monomer mixture of the present invention can be polymerized through irradiation with ultraviolet rays or ionized radiant rays or through the use of a radical polymerization initiator and/or a photopolymerization initiator. Therefore, the monomer mixture per se of the present invention may be used as a raw material for polymerization reactions or may likewise be used in a variety of polymerization reaction systems in which unsaturated bonds participate. For instance, the monomer mixture may be used as a copolymerizable component when synthesizing, for instance, unsaturated polyesters, epoxy-acrylate type resins, urethane-acrylate type resins and acrylate resins. In addition, it may be used as a reactive diluent for photo-setting resin composition. Moreover, it can provide a hardened film excellent in softness, flexibility, water resistance and electrical insulating properties and can thus be used as, for instance, an overcoating agent, an ink, paint and varnishes and a surface-treating agent.

The polymer obtained from the monomer mixture of the present invention which does not contain any free hydroxyl group has markedly improved physical properties such as heat resistance, resistance to impact and mechanical strength. Moreover, the polymer obtained from the monomer mixture of the present invention which has free hydroxyl groups is hydrophilic and excellent in adhesiveness, coating properties and dyeability. Moreover, desired characteristic properties can be imparted to the polymer by reacting the hydroxyl groups of the monomer mixture with various kinds of reactants which are reactive to these groups.

The polymers obtained by polymerization of the monomer mixture according to the present invention are quite useful as, for instance, a variety of optical resin materials, in particular, polymers for plastic lenses.

We claim:

1. A monomer mixture obtained by subjecting a dimer diol/trimer triol mixture selected from the group consisting of
    (a) dimer diol/trimer triol mixtures each substantially consisting of dimer diols and trimer triols which are prepared by polymerizing an unsaturated compound selected from the group consisting of fatty acids having, in the molecule, one carboxyl group and 1 to 4 double bonds and having 11 to 22 carbon atoms and lower alkyl esters thereof to give dimers and trimers and then converting, into hydroxyl group, the carboxyl group (or the lower alkyl ester group in case of the lower alkyl esters) of the resulting dimers and trimers through reduction and having a weight ratio: dimer diol/trimer triol ranging from 30/70 to 99/1; and
    (b) mixtures each substantially comprising dimer diols and trimer triols which are prepared by polymerizing an unsaturated compound selected from the group consisting of aliphatic alcohols having, in the molecule, one hydroxyl group and 1 to 4 double bonds and having 11 to 22 carbon atoms and having a weight ratio: dimer diol/trimer triol ranging from 30/70 to 99/1, to an esterification reaction with an α, β-unsaturated carboxylic acid or to a transesterification reaction with a lower alkyl ester of an α, β-unsaturated carboxylic acid.

2. The monomer mixture of claim 1 wherein the unsaturated compound in (a) and (b) is a mixture of an unsaturated compound having one double bond in the molecule and an unsaturated compound having 2 to 4 double bonds in the molecule and the iodine value of the mixture ranges from 30 to 130 g (iodine)/100 g.

3. The monomer mixture of claim 1 wherein the dimer diol in (a) and (b) is a linear dimer diol/cyclic dimer diol mixture having a weight ratio ranging from 51/49 to 90/10.

4. The monomer mixture of claim 1 wherein the iodine value of the dimer diol/trimer triol mixture ranges from 0.01 to 97.6 (iodine) g/100 g.

5. The monomer mixture of claim 1 wherein the α, β-unsaturated carboxylic acid is an α, β-unsaturated carboxylic acid having 3 to 8 carbon atoms or a lower alkyl ester thereof.

6. The monomer mixture of claim 1 wherein 0.33 to 5 equivalent of the α, β-unsaturated carboxylic acid is reacted with the dimer diol/trimer triol mixture, per one equivalent of the hydroxyl group of the mixture.

7. The monomer mixture of claim 1 wherein substantially all of the hydroxyl groups of the dimer diol/trimer triol mixture are esterified with an α, β-unsaturated carboxylic acid.

8. The monomer mixture of claim 1 wherein the hydroxyl value of the monomer mixture ranges from 0.1 to 134 KOH mg/g.

9. A monomer mixture having a hydroxyl value ranging from 0 to 134 KOH mg/g, obtained by polymerizing a mixed raw material of an unsaturated compound selected from the group consisting of fatty acids having one carboxyl group and one double bond in the molecule and having 11 to 22 carbon atoms and lower alkyl esters thereof with an unsaturated compound selected from the group consisting of fatty acids having one carboxyl group and 2 to 4 double bonds in the molecule and having 11 to 22 carbon atoms and whose iodine value ranges from 30 to 130 g (iodine)/100 g to give dimers and trimers, then converting the carboxyl groups (or the lower alkyl ester group in case of the lower alkyl esters) present in the resulting dimers and trimers into hydroxyl groups through reduction to give a mixture substantially consisting of dimer diols and trimer triols, and then subjecting the mixture having a dimer diol/trimer triol weight ratio ranging from 30/70 to 99/1 to an esterification reaction with an α, β-unsaturated carboxylic acid or a transesterification reaction with a lower alkyl ester of α, β-unsaturated carboxylic acid.

10. The monomer mixture of claim 9 wherein substantially all of the hydroxyl groups present in the dimer diol/trimer triol mixture are subjected to the esterification reaction with the α, β-unsaturated carboxylic acid or the transesterification reaction with the lower alkyl ester of α, β-unsaturated carboxylic acid.

11. A monomer mixture obtained by subjecting a dimer diol mixture selected from the group consisting of
(a) mixtures each substantially consisting of a dimer diol prepared by polymerizing an unsaturated compound selected from the group consisting of fatty acids having, in the molecule, one carboxyl group and 1 to 4 double bonds and having 11 to 22 carbon atoms and lower alkyl esters thereof to give dimers and then converting, into hydroxyl groups, the carboxyl groups (or the lower alkyl ester groups in case of the lower alkyl esters) of the resulting dimers through reduction; and
(b) mixtures each substantially consisting of a dimer diol prepared by polymerizing an unsaturated compound selected from the group consisting of aliphatic alcohols having, in the molecule, one hydroxyl group and 1 to 4 double bonds and having 11 to 22 carbon atoms, to an esterification reaction with an α, β-unsaturated carboxylic acid or to a transesterification reaction with a lower alkyl ester of an α, β-unsaturated carboxylic acid.

12. The monomer mixture of claim 11 wherein the unsaturated compound in (a) and (b) is a mixture of an unsaturated compound having one double bond in the molecule and an unsaturated compound having 2 to 4 double bonds in the molecule and the iodine value of the mixture ranges from 30 to 130 g (iodine)/100 g.

13. The monomer mixture of claim 11 wherein the dimer diol is a linear dimer diol/cyclic dimer diol mixture having a weight ratio ranging from 50/50 to 80/20.

14. The monomer mixture of claim 11 wherein the iodine value of the dimer diol mixture ranges from 0.01 to 97.6 (iodine) g/100 g.

15. The monomer mixture of claim 11 wherein the α, β-unsaturated carboxylic acid is an α, β-unsaturated carboxylic acid having 3 to 8 carbon atoms or a lower alkyl ester thereof.

16. The monomer mixture of claim 11 wherein 0.33 to 5 equivalent of the α, β-unsaturated carboxylic acid is reacted with the dimer diol mixture, per one equivalent of the hydroxyl group of the mixture.

17. The monomer mixture of claim 11 wherein substantially all of the hydroxyl groups of the dimer diol mixture are esterified with an α, β-unsaturated carboxylic acid or subjected to transesterification with a lower alkyl ester of an α, β-unsaturated carboxylic acid.

18. The monomer mixture of claim 11 wherein the hydroxyl value of the monomer mixture ranges from 2 to 134 KOH mg/g.

19. A method for preparing a monomer mixture comprising the steps of polymerizing an unsaturated compound selected from the group consisting of fatty acids having, in the molecule, a carboxyl group and 1 to 4 double bonds and having 11 to 22 carbon atoms and lower alkyl esters thereof to give a low molecular weight mixture;
then distilling the low molecular weight mixture to substantially remove the unreacted substances and to thus give a mixture substantially consisting of dimers and trimers;
converting, into hydroxyl groups, the carboxyl groups (or the lower alkyl ester groups in case of the lower alkyl esters) of the resulting dimers and trimers through reduction to thus give a mixture substantially consisting of dimer diols and trimer triols and having a weight ratio: dimer diol/trimer triol ranging from 30/70 to 99/1; and
subjecting the mixture to an esterification reaction with an α, β-unsaturated carboxylic acid or to a transesterification reaction with a lower alkyl ester of an α, β-unsaturated carboxylic acid.

20. A monomer mixture having the identifying characteristics of a monomer mixture obtained by subjecting a dimer diol/trimer triol mixture selected from the group consisting of
(a) dimer diol/trimer triol mixtures each substantially consisting of dimer diols and trimer triols which are prepared by polymerizing an unsaturated compound selected from the group consisting of fatty acids having, in the molecule, one carboxyl group and 1 to 4 double bonds and having 11 to 22 carbon atoms and lower alkyl esters thereof to give dimers and trimers and then converting, into hydroxyl group, the carboxyl group (or the lower alkyl ester group in case of the lower alkyl esters) of the resulting dimers and trimers through reduction and having a weight ratio: dimer diol/trimer triol ranging from 30/70 to 99/1; and
(b) mixtures each substantially comprising dimer diols and trimer triols which are prepared by polymerizing an unsaturated compound selected from the group consisting of aliphatic alcohols having, in the molecule, one hydroxyl group and 1 to 4 double bonds and having 11 to 22 carbon atoms and a weight ratio: dimer diol/trimer triol ranging from 30/70 to 99/1, to an esterification reaction with an α, β-unsaturated carboxylic acid, or to a transesterification reaction with a lower alkyl ester of an α, β-unsaturated carboxylic acid.

21. The monomer mixture of claim 20, wherein the unsaturated compound in (a) and (b) is a mixture of an unsaturated compound having one double bond in the molecule and an unsaturated compound having 2 to 4 double bonds in the molecule and the iodine value of the mixture ranges from 30 to 130 g (iodine)/100 g.

22. A monomer mixture having a hydroxyl value ranging from 0 to 134 KOH mg/g, having the identifying characteristics of a monomer mixture obtained by polymerizing a mixed raw material of an unsaturated compound selected from the group consisting of fatty acids having one carboxyl group and one double bond in the molecule and having 11 to 22 carbon atoms and lower alkyl esters thereof with an unsaturated compound selected from the group consisting of fatty acids having one carboxyl group and 2 to 4 double bonds in the molecule and having 11 to 22 carbon atoms and whose iodine value ranges from 30 to 130 g (iodine)/100 g to give dimers and trimers, then converting the carboxyl groups (or the lower alkyl ester group in case of the lower alkyl esters) present in the resulting dimers and trimers into hydroxyl groups through reduction to give a mixture substantially consisting of dimer diols and trimer triols, and then subjecting the mixture having a dimer diol/trimer triol weight ratio ranging from 30/70 to 99/1 to an esterification reaction with an α, β-unsaturated carboxylic acid or a transesterification reaction with a lower alkyl ester of α, β-unsaturated carboxylic acid.

23. The monomer mixture of claim 22, wherein substantially of the hydroxyl groups present in the dimer diol/trimer triol mixture are subjected to the esterification reaction with the α, β-unsaturated carboxylic acid or the transesterification reaction with the lower alkyl ester of α, β-unsaturated carboxylic acid.

24. A monomer mixture having the identifying characteristics of a monomer mixture obtained by subjecting a dimer diol mixture selected from the group consisting of (a) mixtures each substantially consisting of a dimer diol prepared by polymerizing an unsaturated compound selected from the group consisting of fatty acids having, in the molecule, one carboxyl group and 1 to 4 double bonds and having 11 to 22 carbon atoms and lower alkyl esters thereof to give dimers and then converting, into hydroxyl groups, the carboxyl groups (or the lower alkyl ester groups in case of the lower alkyl esters) of the resulting dimers through reduction; and (b) mixtures each substantially consisting of a dimer diol prepared by polymerizing an unsaturated compound selected from the group consisting of aliphatic alcohols having, in the molecule, one hydroxyl group and 1 to 4 double bonds and having 11 to 22 carbon atoms, to an esterification reaction with an α, β-unsaturated carboxylic acid or to a transesterification reaction with a lower alkyl ester of an α, β-unsaturated carboxylic acid.

25. The monomer mixture of claim 24, wherein the unsaturated compound in (a) and (b) is a mixture of an unsaturated compound having one double bond in the molecule and an unsaturated compound having 2 to 4 double bonds in the molecule and the iodine value of the mixture ranges from 30 to 130 g (iodine)/100 g.

26. The monomer mixture of claim 25, wherein the dimer diol is a linear dimer diol/cyclic dimer diol mixture having a weight ratio ranging from 50/50 to 80/20.

27. The monomer mixture of claim 25, wherein the iodine value of the dimer diol mixture ranges from 0.01 to 97.6 (iodine) g/100 g.

* * * * *